(12) United States Patent
Kanarowski

(10) Patent No.: US 9,435,993 B2
(45) Date of Patent: Sep. 6, 2016

(54) THREE DIMENSIONAL MICROSCOPY IMAGING

(71) Applicant: Vutara, Inc., Park City, UT (US)

(72) Inventor: Stan Kanarowski, Park City, UT (US)

(73) Assignee: Bruker Nano, Inc., Billerica, MA (US)

( * ) Notice: Subject to any disclaimer, the term of this patent is extended or adjusted under 35 U.S.C. 154(b) by 206 days.

(21) Appl. No.: 14/224,039

(22) Filed: Mar. 24, 2014

(65) Prior Publication Data

US 2014/0340482 A1    Nov. 20, 2014

Related U.S. Application Data

(60) Provisional application No. 61/804,700, filed on Mar. 24, 2013.

(51) Int. Cl.
| | |
|---|---|
| H04N 15/00 | (2006.01) |
| H04N 5/77 | (2006.01) |
| G02B 21/36 | (2006.01) |
| G01N 21/64 | (2006.01) |
| G02B 21/16 | (2006.01) |
| G02B 27/10 | (2006.01) |

(52) U.S. Cl.
CPC ............. *G02B 21/367* (2013.01); *G01N 21/64* (2013.01); *G01N 21/6458* (2013.01); *G02B 21/16* (2013.01); *G02B 27/1066* (2013.01)

(58) Field of Classification Search
CPC .... G02B 21/367; G02B 21/06; H04N 5/265; H04N 5/374; H04N 5/3532; H04N 13/0246
USPC ........ 348/46, 42, 47, 49; 386/223, 224, 323, 386/341
See application file for complete search history.

(56) References Cited

U.S. PATENT DOCUMENTS

| | | |
|---|---|---|
| 644,992 A1 | 9/2002 | Kuavar et al. |
| 7,045,362 B2 | 5/2006 | Hartwich et al. |
| 7,498,551 B2 | 3/2009 | Werner et al. |

(Continued)

FOREIGN PATENT DOCUMENTS

| | | |
|---|---|---|
| WO | WO 2008/091296 A2 | 7/2008 |
| WO | WO 2012/168065 | 12/2012 |

OTHER PUBLICATIONS

Hess et al.; "Dynamic clustered distribution of hemagglutinin resolved at 40 nm in living cell membranes discriminates between raft theories." Proc Nat Acad Sci. Oct. 30, 2007;104(44):17370-5.

(Continued)

*Primary Examiner* — Robert Chevalier
(74) *Attorney, Agent, or Firm* — Thorpe North & Western, LLP

(57) ABSTRACT

A system and method for creating three dimensional images using probe molecules is disclosed and described. A sample is mounted on a stage. The sample has a plurality of probe molecules. The sample is illuminated with light, causing the probe molecules to luminesce. The probe luminescence can be split into at least four paths corresponding to at least four detection planes corresponding to object planes in the sample. The at least four detection planes are detected linearly via an sCMOS camera. Object planes in corresponding recorded regions of interest are recorded in the camera. A signal from the regions of interest is combined into a three dimensional image.

31 Claims, 9 Drawing Sheets

(56) References Cited

U.S. PATENT DOCUMENTS

| | | | |
|---|---|---|---|
| 7,539,115 B2 | 5/2009 | Hell | |
| 7,772,569 B2 | 8/2010 | Bewersdorf et al. | |
| 8,212,866 B2 | 7/2012 | Lemmer et al. | |
| 8,217,992 B2 | 7/2012 | Bewersdorf et al. | |
| 8,610,086 B2 | 12/2013 | Wolleschensky et al. | |
| 8,625,863 B2 | 1/2014 | Enderlein | |
| 8,994,807 B2 * | 3/2015 | Bennett | 348/46 |
| 2011/0234757 A1 | 9/2011 | Zhang et al. | |
| 2011/0267688 A1 | 11/2011 | Kleppe et al. | |
| 2012/0257196 A1 | 10/2012 | Raicu et al. | |
| 2012/0287244 A1 | 11/2012 | Bennett et al. | |
| 2013/0147916 A1 | 6/2013 | Bennett et al. | |
| 2014/0015935 A1 | 1/2014 | Piestun et al. | |
| 2014/0063194 A1 | 3/2014 | Zhuang et al. | |

OTHER PUBLICATIONS

Huang et al.; "Simultaneous multiple-emitter fitting for single molecule super-resolution imaging," Biomed Opt Express. May 1, 2011;2(5), pp. 1377-93.

Jones et al.; "Fast, three-dimensional super-resolution imaging of live cells," Nat Meth. Jun. 2011;8(6):499-505.

Keppler et al; "A general method for the covalent labeling of fusion proteins with small molecules in vivo," Nat Biotech. Jan. 2003;21(1):86-9.

Lemmer et al.; "SPDM: Light microscopy with single-molecule resolution at the nanoscale"; Appl Phys B; 93:1, 2008.

Manley et al.; "High-density mapping of single-molecule trajectories with photoactivated localization microscopy," Nat Meth. Feb. 2008; 5(2): pp. 155-7.

Mlodzianoski et al.; "Experimental characterization of 3D localization techniques for particle-tracking and super-resolution microscopy," Opt Express. May 11, 2009; 17(10), pp. 8264-77.

Shao et al.; "$I^5$ S: Wide-Field Light Microscopy with 100-nm-Scale Resolution in Three Dimensions"; Biophysics Journal; vol. 94, Jun. 2008, 4971-4983.

Shim et al.; "Super-resolution fluorescence imaging of organelles in live cells with photoswitchable membrane probes," Proc Nat Acad Sci. Aug. 28, 2012; 109(35): pp. 13978-83.

Shroff et al.; "Live-cell photoactivated localization microscopy of nanoscale adhesion dynamics," Nat Meth, May 2008; 5(5): pp. 417-23.

Smith et al.; "Fast, single-molecule localization that achieves theoretically minimum uncertainty," Nat Meth. May 2010; 7(5), pp. 373-5.

Zhu et al.; "Wave-front generation of Zernike polynomial modes with a micromachined membrane deformable mirror," Appl Opt. Oct. 1, 1999; 38(28), pp. 6019-26.

Juette et al, "Three-dimensional sub-100nm resolution fluorescence microscopy of thick samples", Nature Methods, Jun. 2008, pp. 527-529, vol. 5, No. 6, Nature Publishing Group.

Kim et al, "Three-dimensional tissue cytometer based on high-speed multiphoton microscopy", Cytometry Part A, Oct. 2007, pp. 991-1002, vol. 71A, No. 12.

Prabhat et al, "Simultaneous Imaging of Different Focal Planes in Fluorescence Microscopy for the Study of Cellular Dynamics in Three Dimensions", IEEE Transactions on Nanobioscience, Dec. 2004, pp. 237-242, vol. 3, No. 4, IEEE Service Center, Piscataway, NY, USA.

Prabhat et al, "Simultaneous imaging of several focal planes in fluorescence microscopy for the study of cellular dynamics in 3D", Progress in Biomedical Optics and Imaging SPIE, Jan. 2006, pp. 60900L-1, vol. 6090, International Society for Optical Engineering, Bellingham, WA, USA.

Toprak et al, Three-Dimensional Particle Tracking via Bifocal Imaging, Nano Letters, Jul. 2007, pp. 2043-2045, vol. 7, No. 7, American Chemical Society.

* cited by examiner (A)

(B)

THREE DIMENSIONAL MICROSCOPY IMAGING

RELATED APPLICATION

This application claims the benefit of U.S. Provisional Patent Application Ser. No. 61/804,700, filed on Mar. 24, 2013, the entire contents of which are incorporated herein by reference.

FIELD OF THE INVENTION

This invention relates to microscopy. More specifically, the invention relates to super resolution microscopy and the creation of three dimensional images obtainable therewith. Therefore, the present invention relates generally to the fields of physics, optics, chemistry and biology.

BACKGROUND OF THE INVENTION

Until about a decade ago, resolution in far-field light microscopy was thought to be limited to 200-250 nanometers in the focal plane, concealing details of sub-cellular structures and constraining its biological applications. Breaking this diffraction barrier by the seminal concept of stimulated emission depletion ("STED") microscopy has made it possible to image biological systems at the nanoscale with light. STED microscopy and other members of reversible saturable optical fluorescence transitions ("RESOLFT") family achieve a resolution greater than 10-fold beyond the diffraction barrier by engineering the microscope's point-spread function ("PSF") through optically saturable transitions of the (fluorescent) probe molecules.

However, slow progress in 3D super-resolution imaging has limited the application of previously available techniques to two-dimensional ("2D") imaging. The best 3D resolution until recently had been 100 nanometers axially at conventional lateral resolution. 4Pi microscopy achieved this through combination of two objective lenses of high numerical aperture, in an interferometric system. 4Pi microscopy was only recently shown to be suitable for biological imaging. Only lately the first 3D STED microscopy images have been published exceeding this resolution moderately with 139 nanometer lateral and 170 nanometer axial resolutions. While this represents a 10-fold smaller resolvable volume than provided by conventional microscopy, it is still at least 10-fold larger than a large number of sub-cellular components, for example synaptic vesicles.

Current understanding of fundamental biological processes on the nanoscale (e.g., neural network formation, chromatin organization) is limited because these processes cannot be visualized at the necessary sub-millisecond time resolution. Current biological research at the sub-cellular level is constrained by the limits of spatial and temporal resolution in fluorescence microscopy. The diameter of most organelles is below the diffraction limit of light, limiting spatial resolution and concealing sub-structure. Although recent developments have improved spatial resolution and even overcome the traditional diffraction barriers, comparable improvements in temporal resolution are still needed.

Particle-tracking techniques can localize small objects (typically less than the diffraction limit) in live cells with sub-diffraction accuracy and track their movement over time. But conventional particle-tracking fluorescence microscopy cannot temporally resolve interactions of organelles, molecular machines, or even single proteins, which typically happen within milliseconds. The spatial localization accuracy of single particles in a fluorescence microscope is approximately proportional to spatial resolution divided by the total number of detected fluorescence photons from the particle in the absence of background and effects due to finite pixel size. For longer acquisition times more signal can be accumulated, hence increased temporal resolution requires a trade-off of decreased spatial localization accuracy. For bright organelles containing a few hundred fluorescent molecules, (or future fluorescent molecules with increased brightness), sufficient signal can be accumulated quickly. However, especially for 3D localization where data acquisition is far more complicated than in 2D, technical constraints arising from axial scanning and/or camera readout times limit the recording speed, and therefore, the temporal resolution. Furthermore, results from axial scanning devices can taint detection processes and give at least a somewhat unclear or imprecise result.

SUMMARY OF THE INVENTION

Thus, there is a need for a microscopy system that can provide 3D imaging with resolution below 100 nanometers in all three dimensions. Another need is directed to achieving particle-tracking in 3D with a temporal resolution below 1 millisecond for enabling visualization of dynamic sub-cellular processes. The inventors have recognized a need for a microscopy system that can be used for three dimensional imaging without scanning. The present invention is directed to satisfying one or more of these needs and solving other problems.

In light of the problems and deficiencies noted above, the present invention provides microscopy systems and methods for creating three dimensional images using probe molecules. In accordance with one embodiment, a method is provided for creating three dimensional images using probe molecules. A sample having a plurality of probe molecules may be mounted on a stage. The sample may be illuminated with light to cause probe luminescence. The probe luminescence may be split into at least four paths corresponding to at least four detection planes corresponding to object planes in the sample. The at least four detection are detected as a linear array via an sCMOS detector or sCMOS camera. Object planes in corresponding recorded regions of interest are linearly recorded in the camera. In other words, the object planes are recorded for corresponding linear recording regions of interest of the sCMOS detector. A signal from the regions of interest can be combined into a three dimensional image.

In one aspect, detecting the at least four detection planes via the sCMOS detector comprises detecting each detection plane in a different linear region of the sCMOS detector.

In one aspect, the method may include dichroically separating the probe luminescence into at least two wavelengths of light prior to or after splitting the probe luminescence, and wherein a first at least two of the at least four paths into which the probe luminescence is split correspond to a first wavelength of the at least two wavelengths, and a second at least two paths of the at least four paths into which the probe luminescence is split correspond to a second wavelength of the at least two wavelengths.

In one aspect, illuminating the sample with light further comprises illuminating the sample with an activation light to activate at least one subset of the plurality of probe molecules, and subsequently illuminating the sample with an excitation light to cause probe luminescence.

In one aspect, the method includes separately recording the object planes for different regions of the sample and arranging the recording planes for the different regions together as a composite two or three dimensional image based on a color-weighted or different-wave length weighted calibration offset.

In one aspect, the method may include blurring the light using a blurring device between a light source and the stage. For example, the blurring device may include an astigmatic lens configured to rotate about an axis or a rotor configured to rotate and cause movement of a light guide to disrupt the light passing through the light guide.

In accordance with one embodiment, a microscopy system for creating three dimensional images using probe molecules may include a sample stage for mounting a sample; at least one light source configured to cause luminescence in at least one subset of probe molecules; and at least two beam splitters positioned to split a luminescence beam into at least four luminescence beams corresponding to at least two object planes. At least one sCMOS camera may be positioned to linearly detect the at least four luminescence beams and capture a plurality of images. An image construction module may be configured to use a processor to combine the plurality of captured images from the at least four luminescence beams and construct a three dimensional image using the plurality of captured images.

In one aspect, the at least one light source further comprises: at least one activation light source configured to activate the at least one subset of probe molecules; and at least one excitation light source configured to cause excitation and luminescence in the at least one subset of probe molecules.

In one aspect, the system may include an aperture between the sample stage and the sensor for eliminating out of focus light.

In one aspect, the at least two beam splitters may be positioned relative to the sCMOS camera such that the at least four detection planes detected via the sCMOS detector are detected in different linear regions of the sCMOS detector.

In one aspect, at least one of the at least two beam splitters comprises a dichroic beamsplitter for dichroically separating the luminescence into at least two wavelengths of light prior to or after splitting the probe luminescence, wherein a first at least two of the at least four paths into which the probe luminescence is split correspond to a first wavelength of the at least two wavelengths, and a second at least two paths of the at least four paths into which the probe luminescence is split correspond to a second wavelength of the at least two wavelengths.

In one aspect, the system may include an alignment module for arranging separately recorded object planes for different regions of the sample together as a composite two or three dimensional image based on a color-weighted or different-wave length weighted calibration offset using the processor.

In one aspect, the system may further include a blurring device between a light source and the stage for blurring the luminescence. For example, the blurring device may include an astigmatic lens configured to rotate about an axis or a rotor configured to rotate and cause movement of a light guide to disrupt the light passing through the light guide.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION OF EXEMPLARY EMBODIMENTS

Figure 1:
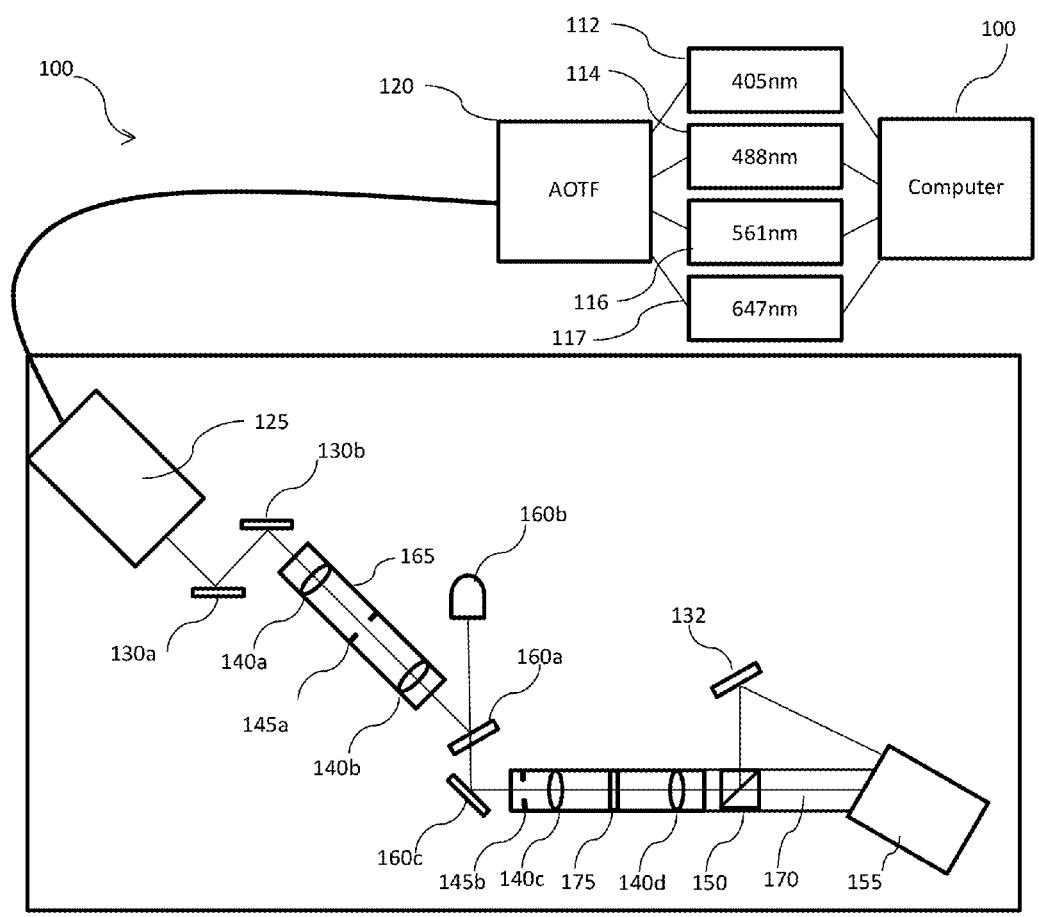
FIGS. 1-2 illustrate microscopy systems for creating three dimensional images using an acoustic optical tunable filter and a total internal reflection fluorescence condenser in accordance embodiments.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Definitions

In describing and claiming the present invention, the following terminology will be used.

The singular forms "a," "an," and "the" include plural referents unless the context clearly dictates otherwise. Thus, for example, reference to "a beam splitter" includes reference to one or more of such devices.

As used herein, the term "plane" is used interchangeably to mean "field." In some cases, which are clear, the term plane refers more specifically to "focal plane." Thus, a linear module utilizes four fields (i.e. quadfield).

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "proximal" refers to the proximity of two structures or elements. Particularly, elements that are identified as being "proximal" may be either in a precise location. Such elements may also be near or close to a location without necessarily being exactly at the location. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

The invention provides for simultaneous, single molecule, multi-channel acquisition of photoactivatable fluorescent proteins in 3-dimensions without scanning. The system utilizes and is capable of switching between TIRF microscopy and Biplane imaging microscopy and when performing all 3 in the same sample, may provide three channel acquisition of both biological and material samples at resolutions far below standard instrumentation, Biplane imaging (20 nm) TIRF (~70 nm-200 nm).

In accordance with an embodiment shown in FIG. 1, a microscopy system 100 is provided for three dimensional, single color, biplane imaging without scanning. A plurality of lasers, such as 405 nm 112, 488 nm 114, 561 nm 116, and 647 nm 117 can be used as light sources. Other wavelengths, numbers of light sources, and types of light sources can also be used. Although specific light sources may be mentioned herein, other types of light sources can also be used to provide the functions of activation and readout as described herein. The 405 nm laser or other lasers can be used to activate a subset of probe molecules. A selected range of intensities can be used to convert only a sparse subset of molecules at a time, e.g. to activate at least one molecule with at least one activation photon. Although powers can vary, a power ranging from about 0.01 µW to 1.0 mW can be suitable in some cases. The power used can depend on the particular probe molecules and sample characteristics. The 488 nm laser is used to detect photoconvertible fluorescent probes in a natural state prior to conversion. The photoconvertible fluorescent probes can exist as green probe molecules prior to conversion. The 561 nm laser has a high power and will, immediately following conversion by the 405 nm laser, excite the converted fluorescent probe, subsequently providing for collection of excitation light by a CCD camera 155. The fluorescent probe can subsequently undergo photobleaching, thus removing the probe from the population. This process, combined with irreversible switchable fluorescent probes, disallows further imaging of these molecules. Typically, high power from the laser can be used to decrease the overall time of the process. Generally, a minimum of 25 mW may be considered. Lower powers can be used, which may increase image acquisition time. Use of a very high powered 561 nm laser, e.g. 200 mW, for example, can result in a considerably more rapid process of excitation, collection and bleaching than may result from a lower powered laser or light source.

Although other probe molecules may be suitable, the probe molecules used herein can generally be fluorophores. The fluorophores can be imaged either sequentially or simultaneously. The system can include a fluorophore localization module configured to localize each fluorophore in three dimensions. The sample can include cells having photoactivatable or photoswitchable fluorescent molecules (PAFMs) residing in a biological membrane, including photoactivatable or photoswitchable fluorescent proteins or photoactivatable or photoswitchable fluorescent lipids or lipids with photoactivatable or photoswitchable fluorescent molecules attached by a chemical bond. In one example, the chemical bond can be a covalent bond. In one optional aspect, the cells can include at least two species of PAFMs to allow simultaneous or subsequent imaging of at least two different subsets of materials. The PAFM may be configured to use Forster resonance energy transfer (FRET) to transfer energy to another probe molecule or to accept energy from another molecule. Broadly, the PAFM can be an energy transfer donor or an energy transfer acceptor.

An acoustic optical tunable filter (AOTF) 120, controllable through software provides the ability to properly attenuate multiple light sources simultaneously and control the efficiency of activation, excitation and bleaching. For example, a 488 nm laser line allows one to image or locate photoactivatable fluorescence proteins prior to conversion by the 405 nm laser, from a visibly green fluorescence to red fluorescence. The AOTF can also control the angle or position of the excitation within the objective back aperture.

The AOTF can provide external control of light source intensity for modulating the light beam. The AOTF can also be used to control the direction or position of the light beam. Software can be used to control the AOTF to vary illumination intensity, direction or position of the light sources independently of any other filters. The AOTF can be configured to control the light sources to provide time-dependent sequences of illumination of at least one wavelength. An optical fiber can connect the light source to the AOTF. An optical fiber combiner can combine the optical power carried by two optical fibers, such as from a plurality of light sources into a single output fiber. The system can also use a total internal reflection fluorescence (TIRF) condenser 125 with existing laser lines. The condenser can include an enclosed box containing a piezo-driven motor allowing switching from the critical angle required for TIRF to regular illumination which can penetrate the sample completely and back again.

Still referring to FIG. 1, a TIRF condenser 125 (which may in some cases be located in a microscope stand 160a-c) can be removed to facilitate the use of a field aperture 145a in the excitation pathway. The CCD camera 155 can be removed from the microscope stand to accommodate the use of a 50/50 beam splitter 150 to achieve the 3-dimensional aspect (separation of a transmitted and reflected light path) of biplane image acquisition. Also, a field aperture 145b and band pass filter 175 can be included between the CCD camera and the microscope stand. Three lasers 112, 114, 116, 117 can be used, as described above. The lasers can be useful in conversion of photoactivatable molecules. All three laser lines can be simultaneously delivered to the system in an automated and attenuable manner through existing software. Optics 140a-d can be added in both the excitation and detection paths of the microscope set-up.

The CCD camera can optionally be an electron multiplying charge coupled device (EMCCD) 155. In one alternative aspect, the camera system can comprise a plurality of cameras. An optional external liquid cooler can be used to cool the EMCCD. The liquid cooler can use thermoelectric cooling to cool the EMCCD. The EMCCD can include at least two detection channels. The camera can capture images from a transmitted light channel. In one aspect, the transmitted light can be imaged by differential interference contrast. The camera can capture images of one or more molecules at a single instant or as a function of time. The system can include a particle analysis module in communication with the camera and configured to provide analysis of particle tracking. Photoactivatable dyes within a sample can be activated with UV activation. The dyes can be excited to fluoresce by 488 nm or 561 nm light and then bleached. The system and method allow for collection of a dye in three dimensional space over approximately 1 to 2 micron thickness of a sample without scanning.

An optical beam splitter 150 is included to split an optical beam (typically within the detection path) into two beams. For example, the beam splitter can be a 50-50 beam splitter or a polarizing beam splitter. Splitting the beam creates two beams focused in different planes so that different object planes of a sample can be imaged, or rather probe luminescence from the sample originating from different object planes is focused onto the camera and detected and/or captured by the camera. Images from the different object planes can be used to create three dimensional images, using software, firmware, or even hardware. Splitting the beam with the beam splitter can result in two beams having different optical path lengths. The difference in optical path length can be utilized to image the sample at multiple different object planes.

The system can include a plurality of mirrors, 130a-b, 132 to direct a light beam along the light path as illustrated. The various optics, apertures, beam splitters, and so forth used in the system can be installed on a construction rail 165, or a micro-dovetail rail 170, as shown in FIG. 1. The system can be set up on a table 105 or other surface, and may also include a computer 110 having a processor configured to process data and operate the software.

Figure 2:
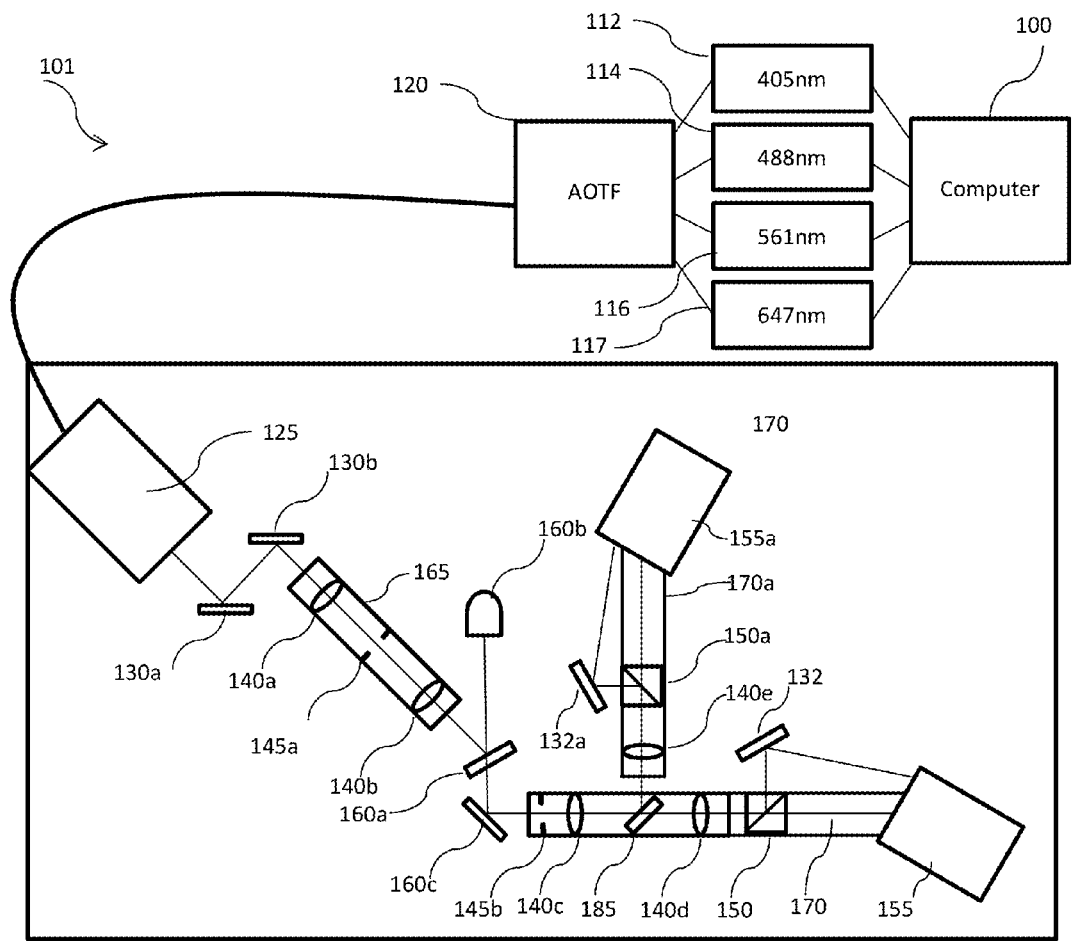

Referring to FIG. 2, a microscopy system 101 is shown which is similar in many regards to the system of FIG. 1. However, FIG. 2 includes a dichroic beam splitter 185 for separating two wavelengths of a light beam. Each wavelength light beam can further be separated by a corresponding 50-50 beam splitter 150, 150a. Additional optics 140e, mirrors 132a, micro-dovetail rails 170a, cameras 155a, etc. can also be optionally used to accommodate and capture the additional beams. In this manner, four beams and four beam paths are created. The system and method allow for three dimensional, simultaneous, two color biplane imaging without scanning. Two photoactivatable dyes within a sample can receive simultaneous UV activation. Further, these two now switched, e.g., activated, dyes can be simultaneously excited. Cameras 155, 155a are used to substantially simultaneously collect images of or luminescence from the 2 dyes in three dimensional space over approximately 1 to 2 microns of depth without scanning. Though the example of FIG. 2 illustrates the creation of four beams along four different beam paths, it is to be understood that the beams may in fact be split any number of times using any suitable combination of beam splitters. For example, the beam may be split into eight different beam paths which may be separated by wavelength, polarization, etc.

Figure 3:
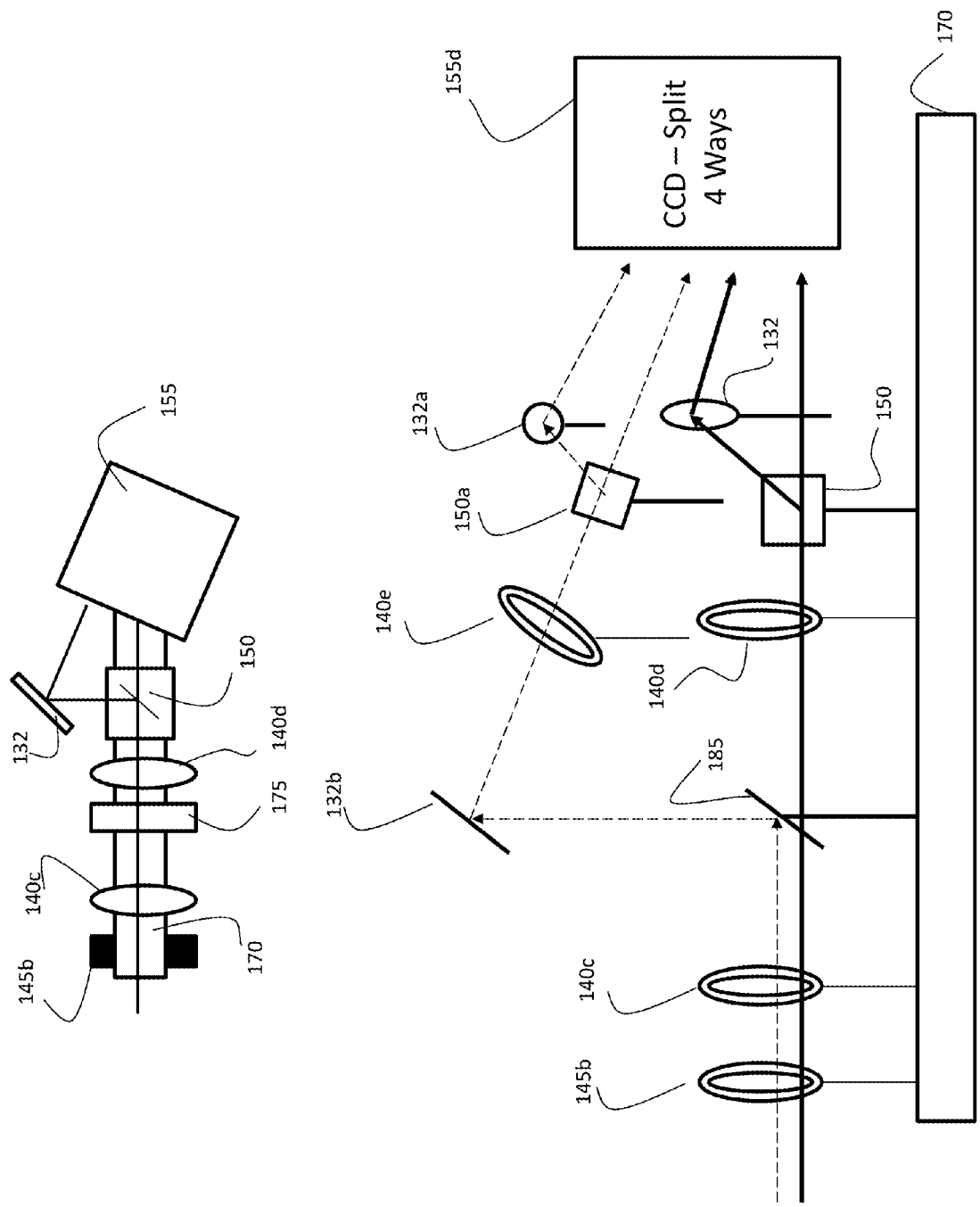
FIG. 3 is a microscopy system for creating multi-color three dimensional images on a single camera in accordance with one embodiment.

FIG. 3 depicts an embodiment of a system for two color, single camera, biplane, three dimensional imaging. The top portion of FIG. 3 is similar to a portion of the system shown in FIG. 1 and is essentially duplicated to achieve the four-way beam splitting shown in the bottom portion of FIG. 3. A dichroic beam splitter 185 is used to separate red and green light from a single light beam into two light beams. Each of these light beams is split using a corresponding beam splitter 150, 150a and imaged on a CCD chip 155d of a camera. The CCD chip can have four regions each for imaging a different input light beam. The system depicted can include an additional mirror 132b and optic 140e above those previously described to facilitate the four way beam split to a single camera chip.

Figure 4:
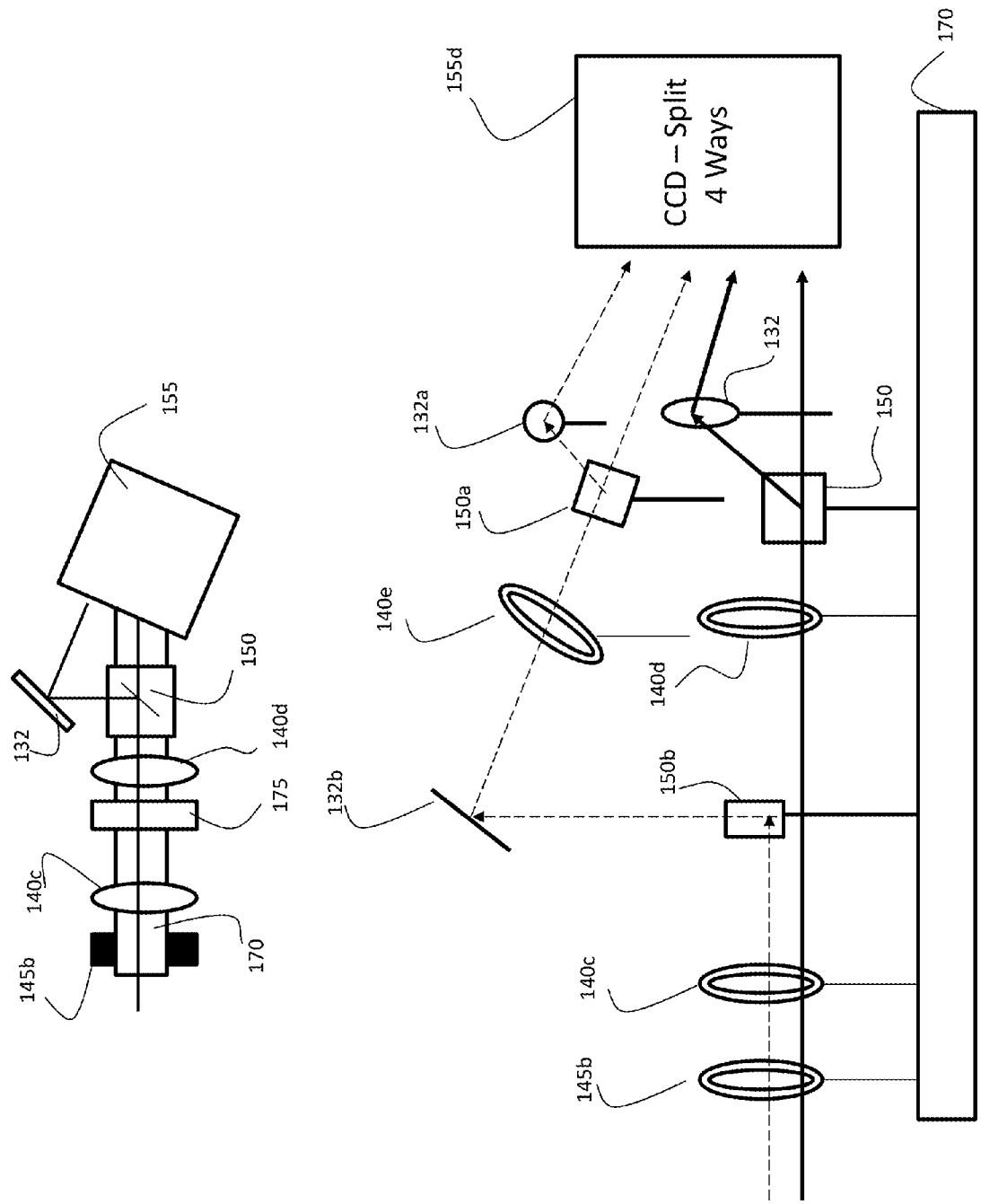
FIG. 4 is a microscopy system for creating four-plane three dimensional images on a single camera in accordance with one embodiment.

FIG. 4 depicts a system similar in many regards to the system shown in FIG. 3. The dichroic lens or beam splitter 185 of FIG. 3 is replaced with a 50-50 beam splitter 150b. This configuration allows for one color, four plane, single camera, three dimensional imaging.

It is noted that in the above embodiments using a beam splitter that beam path bifurcation can be used to allow imaging of probe molecules over a thick section sample without scanning.

A field aperture can be included in the system to block parts of the sample from excitation light or radiation. This reduces background noise and also avoids activation and bleaching of areas of the sample that are not meant to be imaged at that time point. It also reduces overlap between different regions of interest (ROIs) if a camera chip is shared to image several sample planes simultaneously in the multi-plane arrangement. Without the field aperture, parts of the sample may be excited and bleached before equipment or a user is able to measure luminescence. Further such luminescence can be ambient and disrupt the quality of image or detected luminescence of a target area of the sample.

A beam steering device or a sample movement device (which in one aspect may be a sample stage) can be used to move the activation/excitation beam up or down along the sample to image other portions of the sample. In one aspect, the beam may be steered up or down approximately one micron at a time and can image in one dimension as much as six microns or more of a sample. The system and method are able to process an entire 1 to 2 micron section of a sample all at once without scanning. Further, imaging at a depth can be accomplished by moving a stage and without scanning.

Previous methods of imaging thick optical sections of samples included scanning and stacking images. When stacking images, the focal point is not changed and resolution is lost. When moving up and down in a sample, more distortion is created. For example, what may actually be a spherical object may appear elliptical due to distortion through scanning and stacking. Therefore, the approach described herein can typically avoid many of these imaging artifacts.

With use of the TIRF condenser, one additional channel can be imaged Additionally, one could use TIRF illumination combined with biplane detection. This would allow background reduction while allowing for 3D biplane imaging. Also, it is noteworthy that with the TIRF condenser, it is not required that photoactivatable probes be used. Any fluorescent probe may be used.

The system can include an image construction module. The image construction module can include circuitry or a processor and software. The image construction module can be built integrally with the microscope system or separately. The image construction module can take captured images from different focal planes or object planes and combine them to produce a three dimensional image output. The images acquired by the camera can be constructed by the image construction module in real time to provide a real time three dimensional display of combined captured images. An image acquisition module can be used to automatically monitor the fluorescence images, and automatically trigger image acquisition when a number of active fluorophores per time is between predetermined thresholds. The image construction module can be configured to analyze images from the camera and to calculate at least one of a total florescence and a number of pixels over a threshold fluorescence value within a user defined region of interest, generating a single scalar value varying with time.

While some of the dyes discussed herein are photoactivatable, meaning they are first activated and then excited, it is to be understood that non-photoactivatable dyes which are driven into a dark state and then imaged when they reappear from the dark state can also be used. Single step dyes or probes may also be used. For example, a single step dye may be used which is activated/excited and bleached in one step. While dyes discussed herein have included red and green colors, it is to be understood that dyes can be in many different colors. A suitable laser or light source at a corresponding wavelength may be used to activate and/or excite the colors being used.

In one embodiment, an optical microscope system with heightened resolution and capable of providing three dimensional images is provided. Though the following discussion does not reference a particular individual figure, the system described may be understood by reference to the include drawings and to the above descriptions of embodiments. The microscope system can include a sample stage for mounting a sample having a plurality of probe molecules. A light source, such as a non-coherent or coherent light source may be used to illuminate the sample. At least one lens can be configured to direct a beam of light from the at least one non-coherent light source toward the sample causing the probe molecules to luminesce. A camera can detect luminescence from the probe molecules and a light beam path modification module can alter a path length of the probe molecule luminescence to allow camera luminescence detection at a plurality of object planes. The system can also include a field aperture configured to restrict the light beam to limit a number of probe molecules caused to luminesce. An acoustic optical tunable filter can be configured to fine tune a power of the light source. A focusing module can be used to automatically maintain a plane of focus of the light source within the sample.

In one aspect, the light beam path modification module can be a beam splitter configured to split the probe molecule luminescence into at least two beam paths. In this example the camera can be configured to detect the probe molecule luminescence from the at least two beam paths. The beam splitter can be a dichroic beam splitter for dichroically separating the probe luminescence into at least two wavelengths of light prior to or after splitting the probe luminescence. A first path of the at least two paths into which the probe luminescence is split can correspond to a first wavelength of the at least two wavelengths, and a second path of the at least two paths into which the probe luminescence is split can correspond to a second wavelength of the at least two wavelengths. The beam splitter can be a polarizing beam splitter. The beam splitter can be a 50:50 beam splitter. Further, the beam splitter can include a plurality of beam splitters in order to provide imaging of additional focal planes within the sample. The plurality of beam splitters can be any combination of dichroic mirrors, 50:50 beam splitters, and polarizing beam splitters, or other types of beam splitters. For example, the plurality of beam splitters can be a 50:50 beam splitter and two polarizing beam splitters. As another example, the plurality of beam splitters can be two dichroic mirrors. As another example, the beam plurality of beam splitters may include at least one cylindrical lens beam splitter.

In another aspect, and as has been described in greater detail above, the light beam path modification module can comprise at least two beam splitters configured to split the probe molecule luminescence into at least four beam paths. The camera can be configured to detect the probe molecule luminescence from the at least four beam paths.

In another aspect, the light beam path modification module can comprise a linear scanning device configured to scan the sample for probe luminescence at the plurality of object planes for the creation of a three dimensional image with extended axial range.

Other components may be included in the system. For example, a total internal reflection fluorescence condenser (TIRF) or an AOTF can be configured to alter a beam path of the light beam between a region proximal to a side (or periphery) of an objective lens and a region proximal to a center of the objective lens. A widefield microscope stand can be used to support the sample, although other stands can be suitable. An isolation table can be used to reduce vibration of the system and prevent undesirable artifacts from being introduced into the collected data.

In one aspect, the system can include a plurality of light sources and at least one of the plurality of light sources can be a laser. The laser can be a laser capable of exciting two-photon fluorescence or two-photon photochemistry. Non-coherent and coherent light sources can be used in combination. In one aspect, the non-coherent light source can be a point light source. The light source can be an activation light source or a readout light source. The activation and readout light sources can be the same light source or different light sources. The activation and/or readout light sources can be coherent or non-coherent light. The activation and readout light sources do not need to both be coherent or non-coherent light. As described above, a non-coherent light source may comprise an LED or any other type of non-coherent light source. Laser light sources can be used as coherent light sources. In one aspect the laser light source may comprise at least one modulated laser polarization. A plurality of light sources may be used to provide more than one polarization within a sample plane.

A feedback module can be used to provide user feedback triggering image acquisition using an analog voltage representing the total fluorescence output of the camera. In one aspect, the feedback module can include a speaker attached to the voltage to provide audio output as a pitch proportional to the total fluorescence of the image. An analog circuit can be used to generate a TTL logic pulse when the voltage is within a predetermined range. An integrated circuit or voltage comparator can apply the TTL voltage back to the camera to gate image acquisition.

A graphical processing unit (GPU) can be in connection with the fluorophore localization module, and be configured to provide processing for the fluorophore localization module for localizing fluorophores. Further, a graphical user interface can be used to provide an interface for a user to interact with captured images, created three dimensional models, and other data.

In one aspect, the system may include a multi-well plate imaging module configured to automatically move from one sample well to another to image a plurality of sample wells. The multi-well plate imaging module can be configured to automatically translate the sample in any direction to provide optimal imaging. Also, the multi-well plate imaging module can be configured to simultaneously image any number of individual molecules within a single cellular compartment.

Molecule-molecule binding of molecules in the sample can be measured using a molecule-molecule binding measurement module. The sample can optionally include living cells. In some situations, it may be useful to image these cells in various environments and in differing conditions. The system described herein may be used for samples which are in vivo, ex vivo, in vitro, perfused, etc. In one alternative aspect, the sample may be incubated in gas. In the case of a gas-incubated sample, the system can further comprise a gas control module configured to control the gas in which the sample is incubated. To better control the sample environment, the system can include a temperature control module configured to control a temperature of the sample and/or a humidity control module configured to control a humidity of the sample.

The system can include a conventional microscope for simultaneous or sequential imaging of the sample. Alternately, or additionally, the system can include an electron microscope configured to acquire electron microscope images of the sample simultaneously or sequentially with the camera. Some examples of contemplated electron microscopes include a scanning electron microscope (SEM) and a transmission electron microscope (TEM).

The cameras used in the system can optionally be cooled with liquid cooling. An image construction module as used herein can be circuitry or a processor and software. The image construction module can be built integrally with the microscope system or separately. The image construction module can take captured images from different focal planes or object planes and combine them to produce a three dimensional image output.

The molecular understanding of disease has become of increasing interest in the era of "personalized medicine," including accurate identification of diagnostic/prognostic biomarkers, as well as development of corresponding targeted therapeutics and response monitoring protocols. Treatment of diseases such as breast cancer, atherosclerosis, and Alzheimer's disease has been greatly impacted by the identification of proteomic and genomic signatures. Optical microscopy remains a primary approach for elucidating spatiotemporal behavior of disease-associated biomolecules. Yet, a mismatch has historically existed between the optical diffraction limit (~250 nm), and the scale at which most biochemical process operate (<50 nm). The introduction of "super-resolution" (SR) microscopy (5-7) has eroded this mismatch, allowing optical imaging to enter the nanoscale regime. Broadly speaking, the myriad of optical super-resolution microscopy techniques can be grouped into "Engineered Illumination" and "Single Molecule Localization" (SML) categories. The former includes such modalities as Stimulated Emission Depletion (STED) and Structured Illumination Microscopy (SIM). The latter group includes (Fluorescence) Photoactivated Localization Microscopy ((F)PALM), direct stochastic optical reconstruction (dSTORM), Stochastic Optical Reconstruction Microscopy (STORM), and the numerous variations therein. In the past several years, a number of researchers have reported unique biological insights with the aid of SR microscopy. These include studies of DNA/chromatin structure, fundamental neuronal behavior, cardiovascular applications, and infectious disease mechanisms. While it is expected that "nanoscopy" will become increasingly useful in aiding researchers to formulate new understanding, significant improvements in current commercial technology are sought to increase the utility, flexibility, and resolving power of SR microscopy.

Single Molecule Localization (SML) Super-Resolution (SR) Microscopy approaches rely on imaging a small subset of a sample's fluorophores at a given time. This is generally accomplished via photoswitching or photoactivation, which refer to photochemical processes that render nearly all the sample fluorophores to a dark state while allowing (or activating) a small number to be in the "light" state. These remaining, isolated molecules are then imaged and their location computationally inferred by estimating the most likely position of the emitter based on the position of the recorded point-spread function (PSF). The process is repeated thousands of times to create a map of the locations of nearly every fluorophore in the sample with much higher precision than allowable under normal diffraction-limited conditions. SML-based SR microscopy offers a number of benefits over the Engineered Illumination approaches listed above. Some of these benefits are described below: (1) Simpler illumination requirements than STED: STED (stimulated emission depletion) microscopy involves complex, high quality illumination schemes with extremely high-power depletion intensities. SML approaches involve simpler excitation with >100 fold lower intensity, permitting utilization of less expensive, and less damaging, CW (continuous wave) laser sources. (2) Easier extension to 3D SR than STED: SML-based approaches allow for sub-diffraction localization in all three dimensions. These strategies rely on either non-axially symmetric PSFs; or imaging the sample at two axially separated focal planes, such as the biplane approach. Conversely, commercial implementations of STED microscopy offer resolution enhancement only in the lateral dimensions. (3) Better achievable resolution than Structured Illumination Microscopy (SIM). SIM is only capable of two-fold resolution improvement (down to ~120 nm) over conventional microscopy, representing 2-4 fold worse performance than SML in each dimension. Non-linear effects have been demonstrated to further improve the SIM resolution in proof-of-concept studies but these concepts are far from commercialized realization. However, SML SR microscopy suffers from one major drawback with respect to STED and SIM that limits its current application range: large numbers of recorded images are required to reconstruct a single SR map, thereby limiting temporal resolution. A next generation SML SR microscope, based on the present technology, is capable of dramatically faster performance, enabling simultaneous video-rate nanoscopy of multiple biomolecules, with better overall resolving capacity than current solutions. Temporal resolution can be desirable and can be implemented in a faster SR system, which will extend applicability to a much broader range of biological studies.

Previous studies have shown the feasibility of SML SR microscopy of live/dynamic biological samples. However, multicolor images were acquired as an interleaved sequence, preventing true temporal co-registration between color channels, which is important for dynamic samples. Additionally, the total field of view (FOV) was reduced to about 7×13 µm to achieve the required high frame rates. Furthermore, SML analysis was performed "off-line", preventing real-time display of SR images during raw data acquisition. Subsequent live-cell studies using organelle-specific dyes reported similar spatial resolutions with simultaneous, ratiometric-based dual color imaging. However, temporal resolution was reduced to 1-2 s in this case. The present technology provides a 3D SML super-resolution microscope, capable of (1) 10-15 fold improvement in overall temporal resolution from what has been reported; (2) simultaneous multi-color imaging, while maintaining (3) <50 nm resolution in three dimensions.

The introduction of the electron multiplying charge coupled device (EMCCD) revolutionized the field of single molecule detection with its unprecedented optical sensitivity by using a separate amplification step based on impact ionization. However, no EMCCD with >1 megapixel format is commercially available, thus inherently limiting the available FOV. If an imaging setup requires multiple simultaneous channels (e.g. spectral channels for multi-color applications, focal channels for multi-focal plane approaches) imaged on one chip, the FOV is reduced even further. In addition, EMCCDs can only be read out at moderate frame rates, typically 30-60 frames/s. Faster frame rates are only achievable by reducing the total number of pixels (and thus FOV). For instance, up to 900 Hz image acquisition rate has been recently reported by limiting the FOV to only 64×128 pixels (35). Separately, EMCCDs also suffer from a unique noise source due to the multiplication gain register, adding an additional noise factor that effectively halves the nominal quantum efficiency (QE) of EMCCDs, and thus their overall sensitivity (38).

Recent advances in complementary metal oxide semiconductor (CMOS) based imaging detectors have begun to challenge the primacy of EMCCD use in SML SR microscopy. These "scientific grade" CMOS (sCMOS) detectors offer much larger pixel arrays, up to five megapixels, with relatively low readout noise (1-2 e$^-$) and without the multiplication noise of EMCCDs. Further, due to more flexible readout architecture, overall image acquisition speed is significantly higher than EMCCDs (e.g. one hundred 4-megapixel frames/s).

However, sCMOS technology also presents two unique challenges for use in SML SR microscopy: (1) in contrast to EMCCDs, the read noise and gain factor varies significantly across the pixel array, and as such, may not be considered a constant value for a given pixel. These heterogeneities represent a hindrance to accurate localization of single molecules, as this analysis depends critically on an accurate understanding of photon signal and background in every pixel. These pixel heterogeneities cannot by correctly accounted for by the established statistical methods. To maximize readout speed (and to minimize readout noise), sCMOS are operated in "rolling shutter" mode, whereby each pixel row is separately exposed and digitized in short succession in a wave-like pattern. If multiple imaging channels are used, such as in multi-focal plane or multi-color imaging, there must be clear temporal correspondence between each location in each channel. This effect requires that corresponding features in each image channel must be read at nearly the same instant. The present technology allows for optimal performance of sCMOS based detection, while fully exploiting this technology's speed and sensitivity advantages for SML SR microscopy. The present technology includes an optical design configured to maximize accuracy for 3D multi-color SML SR microscopy with sCMOS cameras by arranging separate image channels in a linear array.

It is noted that in rolling shutter mode, where the shutter rolls or moves across the exposable image area of the sCMOS sensor rather than exposing the image area all at a same time as with a global shutter, there may be a time delay between when an image is captured on one portion of the sensor as compared with when an image is captured on another portion of the sensor. This time delay may be compensated for using a compensation module executed using a processor and a memory of a computing device. For example, if a sensor were divided into 100 lines across which the shutter rolls, a first line (line 1) may be imaged at time 1, a second line (line 2) may be imaged at time 2 and so forth. Compensation for the time delay between lines may include modification of time stamps, adjustment of positioning or coloring of probe molecules in the images that may change during the time delay and so forth. An advantage using a rolling shutter is that the image sensor can continue to gather photons during the acquisition process, thus increasing sensitivity. Compensation for the time delay during the rolling from one portion of the sensor to another may compensate for some of the negative aspects of a rolling shutter, such as wobble, skew, smear or partial exposure, for example.

The localization process inherent to SML SR microscopy may present a computational burden, particularly for rapid analysis and display of dense SR images. In one example, single molecule localization consists of six discrete steps: (i)

image filtering/noise reduction; (ii) particle identification; (iii) region of interest (or cutout) selection; (iv) maximum likelihood estimation (MLE) of molecular positions; (v) localization precision assessment; and (vi) image reconstruction. In typical implementations, MLE of particle locations and the associated precision generally represents the rate-limiting step. In an effort to improve the overall speed of the localization process, implementations based on graphics processing units (GPU) may be utilized. The highly parallel architecture of GPUs is useful for single molecule localization due to the fact that individual localizations can be treated as separate computational tasks. Using this approach, localization rates may be in excess of 200,000 localizations/second. Given that typical SML SR microscopy data contains on the order of 100 molecules per frame, this approach can accommodate at least 1 kHz image acquisition rates in real time. In addition, the introduction of "multi-emitter" MLE methods also provides significant speed increases, with greater flexibility in terms of fluorophore density. Thus, high-quality SR image reconstruction with 8-10 fold less raw data and the associated speed advantage is viable, despite a significant increase in computational burden. Both, GPU-based SML algorithms and multi-emitter fitting are expandable to 3D SML in the case of astigmatic SML SR microscopy. The present technology may implement and commercialize optimized GPU-based algorithms to complement hardware improvements. The present technology enables high speed (up to video rate) analysis and rendering of 3D SML SR images to enable real time data analysis and display.

A high-speed SML SR microscope can be provided which is capable of (1) <50 nm resolution in 3D, (2) video-rate analysis and display of SR images, and (3) simultaneous detection of two or more fluorophore species. Optical design enhancements can be made, including utilization and characterization of novel sCMOS detector technology, as well as development and integration of GPU-enabled 2D and 3D single molecule localization algorithms into a single commercial package.

Figure 5:
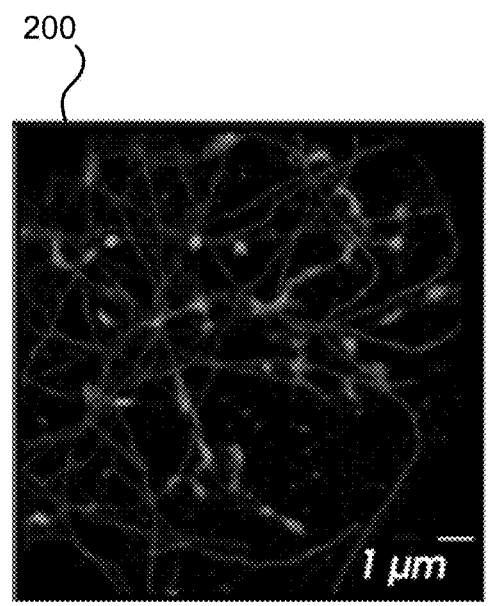
FIG. 5 is a three color SR image of BSC1 cell, showing location of microtubules, mitochondria and clathrin coated pits taken using a biplane microscopy system.

The present technology has been used to implement 3D localization precision of <30 nm in each dimension, with up to four emission colors. FIG. 5 shows an example 3D, three-color SR image 200 of a BSC1 cell, labeled with Alexa Fluor (AF) 647 α-tubulin (red), AF 568 α-clathrin (blue) and ATTO 488 α-TOM 20 mitochondrial protein (green). This image 200 was captured using the systems and methods disclosed herein. In one example, a system of the present technology may allows up to four excitation wavelengths (405, 488, 561, and 647 nm), with simultaneous detection of up to two colors.

The present technology includes improvements which incorporate the latest generation sCMOS cameras or detectors from all major vendors. Such detectors may allow four simultaneous image channels, each comprised of 200×400 pixels, to be read out at 1000 frames/sec (fps), with further FOV (field of view) reductions enabling up to 3000 fps. This represents an order of magnitude increase in FOV with four times the number of imaging channels, while maintaining higher overall raw data acquisition rates compared to that reported previously. Careful optical design is necessary to avoid artifacts. Specifically, sCMOS readout mechanisms can result in each horizontal pixel line being exposed and digitized at slightly different time points. Multiple simultaneous channel acquisition will suffer inaccuracies unless corresponding features in each channel occupy identical rows in the pixel array. As such, the present technology may utilize a multi-color biplane SML SR optical design that results in four image channels (two colors×two focal planes) arranged in a linear array (i.e., 1×4 grid) on a rectangular sCMOS detector (in contrast to other layouts where the four channels may be arranged in a grid or other pattern, such as a 2×2 grid layout to be detected on a square sCMOS detector). Use of a rectangle image sensor or use of a portion of an image sensor, rectangular or otherwise, may reduce processing times such as when the portion of image sensor used is less than the full image sensor because there is less data to process. Where channels are arranged linearly on a rectangular sensor in a rolling shutter mode, because the lines may extend across each of the channels and a height of the image data (the number of lines to record) is reduced because of the linear arrangement, processing times may also be reduced.

Figure 6:
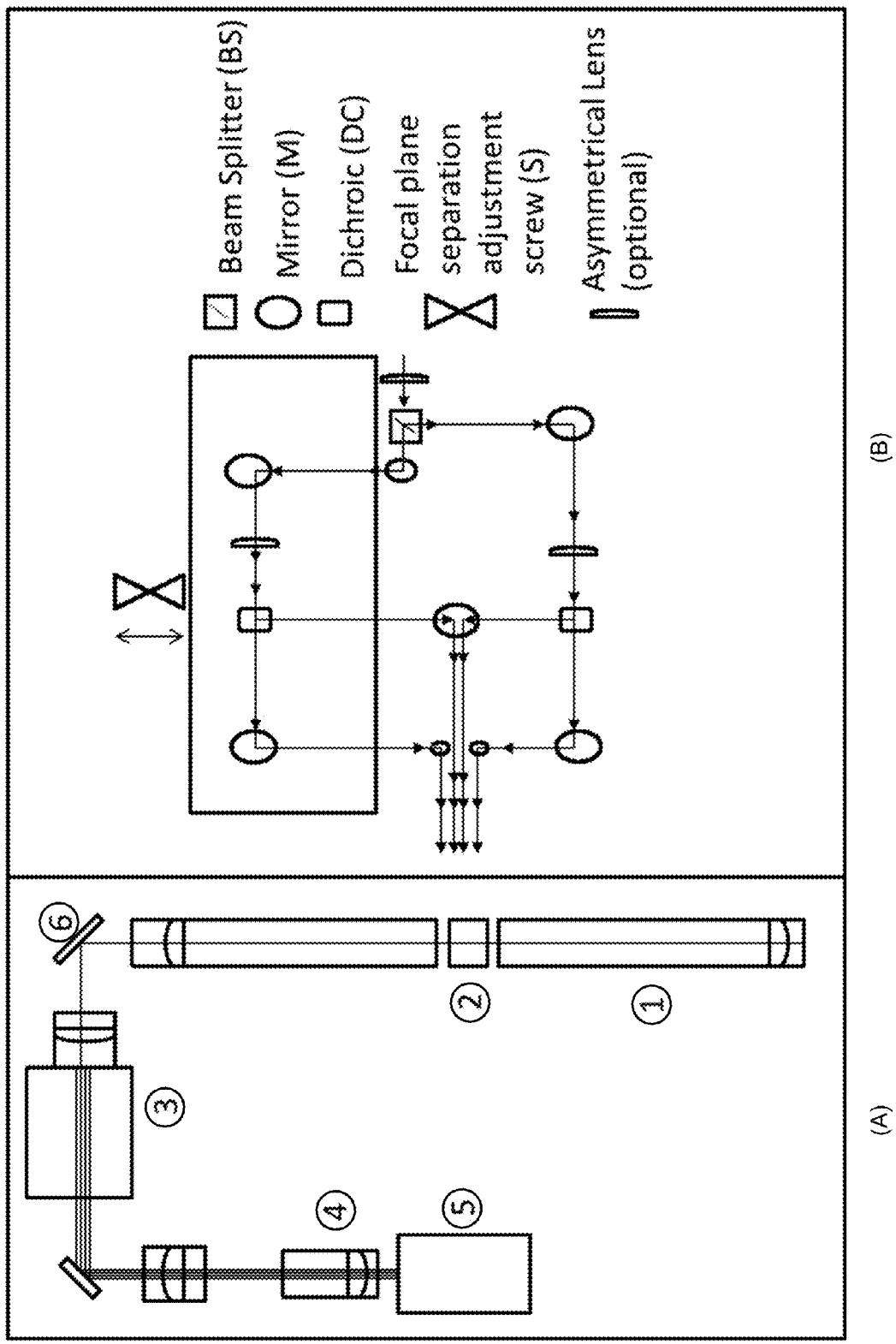
FIG. 6 is a design of a linear biplane microscopy system in accordance with an embodiment.

Reference will now be made to FIG. 6. On the left at (A), a schematic is shown outlining a design of an optimized, aberration-corrected optical detection path 300 suitable for use with the large FOV of the sCMOS detector. The path 300 is illustrated as progressing through the various portions of the system from ① to ⑥. ① represents fluorescence from the sample. ② represents an intermediate image plane with a spatial filter to reduce channel overlap. ③ represents a multi-color biplane module, also shown in greater detail on the right of FIG. 6 at (B). ④ represents final image-forming lenses. ⑤ is an sCMOS detector, such as an ORCA-Flas4.0, Hamamatsu detector. ⑥ represents a mirror located at a conjugate pupil plane. This component can be replaced by a deformable mirco-mirror array to enable optical aberration correction or engineering of the detection path point spread function (PSF).

On the right of FIG. 6 at (B), a design of the present multicolor biplane module is shown. The module is nominally designed to produce image planes with equivalent focal separation of 500 nm, enabling 1-2 μm of 3D SR localization capability. The module divides incoming light by a 50/50 beamsplitter (BS), which is steered by mirrors (M) and separated according to wavelength using dichroics (DC). The result is a linearly arrayed four channel (2 focal planes, 2 colors) image projected onto the sCMOS detector ⑤. The knob at (S) is a screw that may be screwed in and out. Adjustment of the screw (S) results in a repositioning of mirrors (M) by moving or adjusting a base to which the mirrors (M) are attached. Adjustment of the mirrors changes a width of the biplane image. Adjustment of the screw (S) may result in adjustment or movement of fewer than all of the mirrors in FIG. 6 (B), such as by moving mirrors (M), (DC) and (M) shown on an upper half of the image of FIG. 6 (B), while mirrors (M), (DC) and (M) shown on a lower half of the image of FIG. 6 (B) remain stationary. The mirrors moved or adjusted through adjustment of the screw (S) may be moved simultaneously and to a same degree as one another. Considering the direction of the beam path as light enters the module at the right side of FIG. 6 (B) and before the beam is split at the beamsplitter (BS) as horizontal, adjustment of the screw (S) may result in a shortening of the beam path perpendicular to the horizontal direction, which may be considered vertical for purposes of explanation. Shortening of the vertical beam path length may result in a narrowing of a width of the biplane imaging. Conversely, lengthening of the vertical beam path length may result in a widening of a width of the biplane imaging. Furthermore, asymmetrical lenses (L) can be added to induce aberrations such as astigmatism to enable multimodal 3D SML imaging in combination with the biplane detection scheme.

Residual optical aberrations (such as tilt and coma) can reduce localization accuracy. However, inclusion of a deformable mirror can serve as an efficient means to optimize the system's detection PSF. Furthermore, higher power solid state lasers (e.g. Genesis®, Coherent) may be used where sufficient photon emission rates are not be attainable in our existing setups, given potentially short (<1 ms) detector exposure times. Power levels may be optimized, as well as the relationship between power intensity and the rate at which fluorophores can be driven into the dark state vs. the density of the remaining emitters. By initially using higher powers, most of the molecules in the sample can be rendered non-detectable. Then, by decreasing the power 10-40%, the relative fluorophore density may be tuned to optimum levels while maintaining sufficient photon emission rates.

Figure 7:
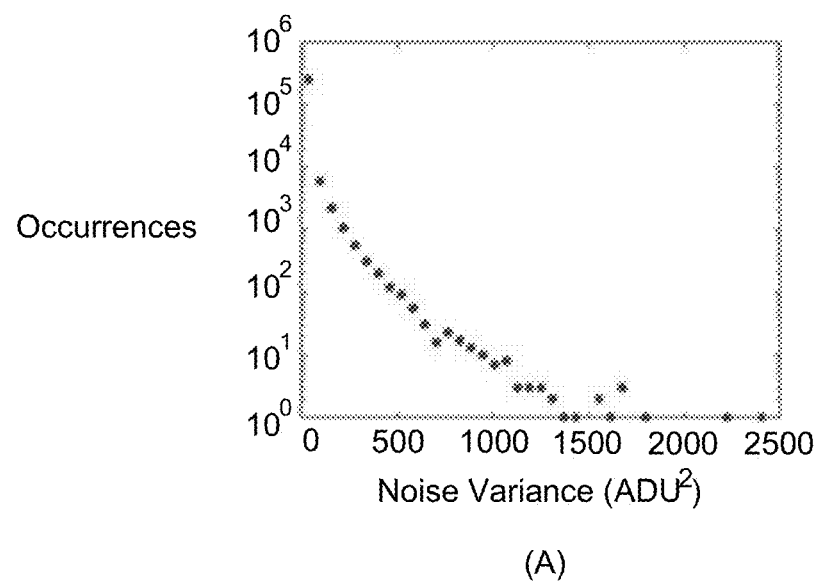
FIG. 7 includes graphs illustrating per-pixel inhomogeneity of sCMOS detected light.
Figure 7:
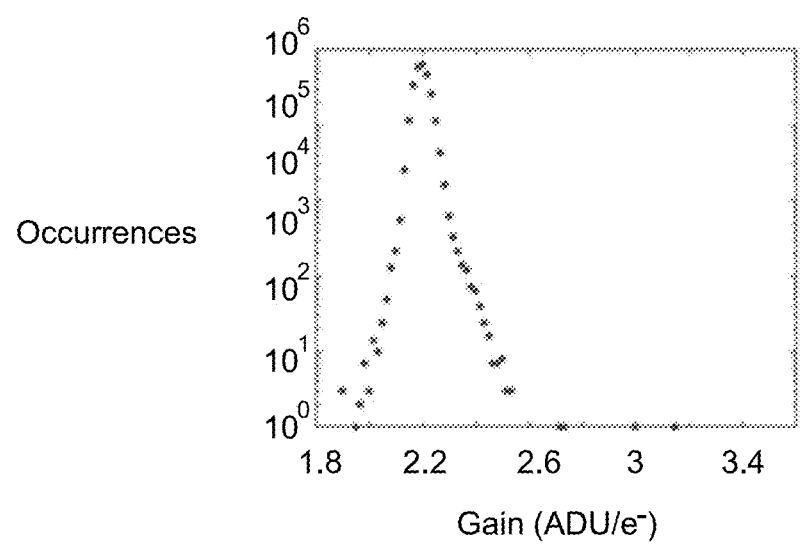

As discussed above, the included sCMOS camera offers a tremendous advantage in overall acquisition speed. However, sCMOS cameras suffer from much greater performance heterogeneity across the detector array than EMCCDs. For instance, an analysis has revealed a large range of pixel to pixel readout noise variance, from tens to thousands of $ADU^2$, as shown in FIG. 7 (A). Furthermore, the calculated gain values vary from 1.9-3.2 ADU/e⁻, as shown in FIG. 7 (B). In-depth analysis of the sCMOS detector may be performed to account for pixel-dependent variations in readout noise, gain, and offset value. To calculate the former and latter parameters, images may be captured with all light blocked to the detector. To calculate the gain (ADU/e⁻) at each pixel, multiple images may be acquired at varying light intensities. A linear least-squares model describing the slope of the noise variance vs. signal will yield the gain at each pixel. Inhomogeneities in the localization algorithm may be accounted for.

The present SML SR system may be used to characterize the diffusion/clustering and internalization behavior of epidermal growth factor receptor (EGFR) molecules on a live cell plasma membrane. EGFR displays well-characterized dynamics that include dimerization and oligomerization upon ligand binding, and internalization via endocytosis. The approach may utilize A431 cells (ATCC), a commonly used cell culture model for EGFR studies due to the high expression level of the receptor. Cells may be exposed to epidermal growth factor (EGF) conjugated to AF 647 or AF 568 dyes (Invitrogen), and DiD or DiI (Invitrogen), membrane-binding fluorescent dyes that each have been demonstrated to exhibit good photoswitching behavior suitable for SR imaging (36). Samples may be imaged at 561 nm and 647 nm excitation simultaneously over 15-30 minutes to allow for imaging of ligand binding, EGFR trafficking/clustering, and endocytosis. This biological model enables optimization of several imaging parameters, such as excitation powers. Furthermore, an optimum number of raw image frames used to construct dynamic SML SR data sets may be calculated. For example, as little as 50-100 raw frames per SR image have been sufficient to reconstruct receptor dynamics on the membrane when using multi-emitter fitting. Use of the membrane-binding DiD or DiI dye may serve as a morphological marker, and will allow visualization of EGFR trafficking within the context of nanoscale cell membrane topography, as well as the endosome/cargo structure. These approaches serve to better understand the trade-off between temporal resolution and adequate spatial sampling for sufficient image quality. In addition, the resulting data may be used for development and testing of more advanced localization algorithms.

The present technology may utilize state of the art SML SR control, acquisition, and analysis software, which when used with computer-implemented localization algorithms and integrated GPU-based localization techniques can enable real-time localization and display during data acquisition with sCMOS detection described above. SML algorithms may be adaptable to the highly parallel architecture of GPUs, with up to $2.6 \times 10^5$ localizations per second. Based on this benchmark, a GPU-based algorithm can allow for real-time localization of fluorophore densities of 0.33 molecule/µm², in good agreement with typical experimental conditions.

Approximately 90% of the computational burden in the analysis algorithm may involve iterative evaluation of the maximum likelihood estimate (MLE) required to infer emitter locations. To improve performance, this process can be implemented on GPU architecture to greatly increase parallel capacity for this step. In addition, as preliminary data indicates, the offset, noise variance, and gain may be evaluated separately for each pixel in the array in order to accurately model sCMOS response. Certain procedures such as particle identification and cutout selection may be more "global" in nature, and thus can remain CPU-based.

While such GPU-based localization has been demonstrated, correction for sCMOS heterogeneities (FIG. 7) has heretofore not been reported. The present technology can use a mathematical basis for the correct statistical treatment of this phenomenon and has shown that localization precision and accuracy at the theoretical limit can be achieved even with sCMOS cameras. To demonstrate the feasibility of this improved treatment, FIG. 8 (A) shows a small sCMOS region indicating a pixel with high noise variance (highlighted portion within the bar of black). These variations result in inaccurate conventional MLE determinations of particle locations, as illustrated in simulated data of fluorescent emitters arranged in two, narrowly separated lines, as in FIG. 8 (B). However, a strict evaluation of the likelihood function describing the number of detected photons as a function of camera parameters presents an additional undue computational burden in the localization algorithm.

Figure 8:
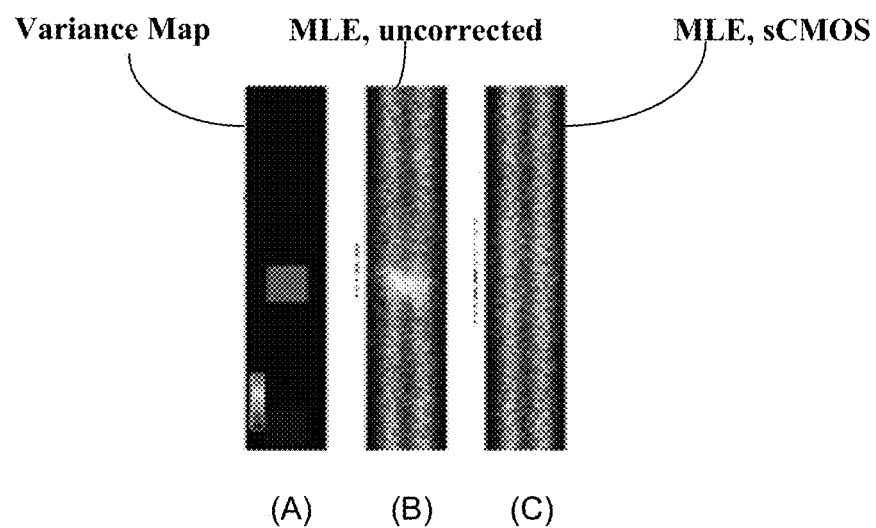
FIG. 8 includes illustrations of sCMOS pixel variance.

A simplified analytical approximation may be used that takes into account both shot noise and the non-negligible readout noise in sCMOS cameras. Briefly, although the readout noise can be described as Gaussian, for sufficiently high photon counts ($\sim 10^2$-$10^3$ per pixel), the photon statistics can accurately be approximated as following a modified Poisson distribution, expressed as $P(\mu_i + var_i/g_i^2$, where P denotes a Poisson distribution operator, and $\mu_i$, $var_i$, and $g_i$ denote the expected number of photons, the readout noise variance, and gain at the i-th pixel, respectively. Furthermore, this relation is also used to evaluate the fluorophore location precision via the Cramér-Rao lower bound (CRLB). Results of this improved treatment are shown in FIG. 8 (C), whereby the correct morphology is reproduced in simulated data, without detector-based artifacts.

The present technology can enable GPU-based 3D systems and software algorithms suitable for biplane detection SML SR microscopy. While GPU algorithms have been demonstrated for astigmatism-based techniques, biplane detection has been shown to display more uniform localization precision across a larger axial range. Using a measured 3D PSF can provide excellent results for this purpose, while accounting for optical aberrations and avoiding artifacts. To characterize the system PSF, 100 nm beads (Tetraspek, Invitrogen) may be imaged which contain fluorescent dyes spanning the optical spectrum. Beads are imaged at each wavelength over a range of focus positions, covering an axial distance of 4-8 µm at 100 nm increments to create a reference 3D PSF. The expected per-pixel photon count will then be interpolated from the measured response using a cubic spline fit. Again, proper characterization of the performance of the sCMOS detector is valuable for each aspect of this approach, in order to accurately determine the photon count distribution across reference and experimental PSFs. Both of these steps is capable of implementation on a GPU platform, thus allowing for a high degree of parallel computation in process. Such a configuration may result in an increase in speed from current CPU-based implementations of 10-100 fold. Alternative approaches have been established to mitigate against unforeseen challenges due to utilization of a measured PSF. For instance, assuming a theoretical PSF for 3D localization is possible, provided the actual system performance is very closely matched to the ideal. To ensure this, a deformable mirror may be incorporated to reduce aberrations in the system via correct implementation of the appropriate linear combination of Zernicke mode(s).

The presence of multiple fluorphores within a single fitting region becomes more likely with higher density. This results in localization artifacts and/or under-utilized data. The present technology implements GPU-based "multi-emitter" fitting algorithms for 2D and 3D localization of multiple fluorophores in a single fitting region. In the 2D Gaussian case, the model describing expected pixel photon counts will be modified to include a linear combination of 5-8 Gaussian functions. Initial 2D studies have been performed with this approach, and the present technology further accounts for sCMOS behavior and GPU implementation. The present technology may utilize a measured 3D PSF, with 3D interpolation within the GPU to extract fluorophore positions, as well as the aforementioned sCMOS pixel correction. The generalized algorithm to implement multi-emitter fitting will be as follows: an MLE determination, with associated p-value, of fluorophore locations is made assuming progressively increasing numbers of fluorophores within a given cutout region. This provides an assessment of the most likely number of emitters. This approach also includes the initial localization guess for the $N^{th}$ emitter, obtained via subtraction of the previous model assuming N−1 emitters, and rejection of emitters that likely lie beyond the fit neighborhood. Further, overlapping fit regions will be accounted for to avoid repeated localization of identical molecules. Despite the higher computational burden required for multi-emitter localization, faster overall image analysis can be achieved due to GPU implementation, as well as fewer images needed to localize an equivalent number of molecules. To mitigate this effect, the maximum number of emitters allowable in this algorithm may be optimized to balance computational time vs. data utilization.

Figure 9C:
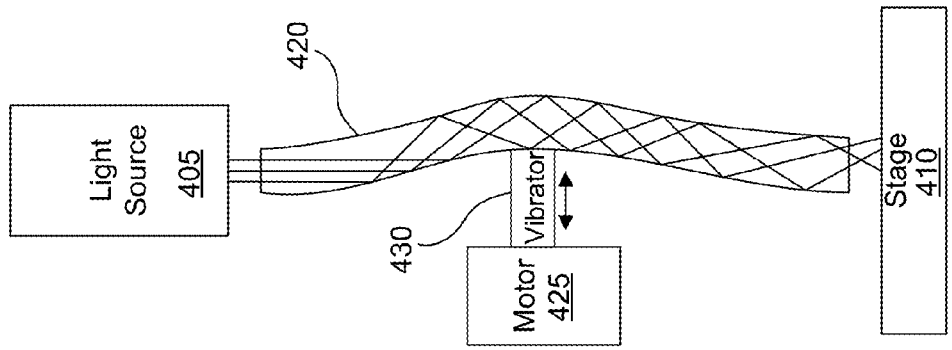
FIGS. 9a-9c illustrate example implementations of a system, with FIGS. 8a and 8c particularly being configured to reduce image speckle resulting from use of coherent light sources.
Figure 9B:
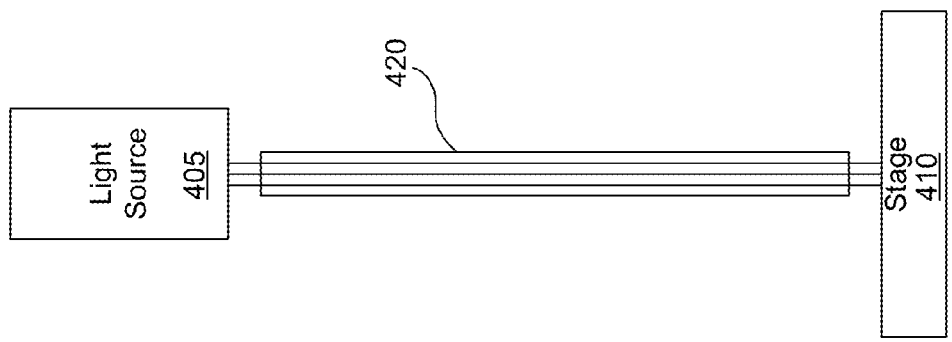
Figure 9A:
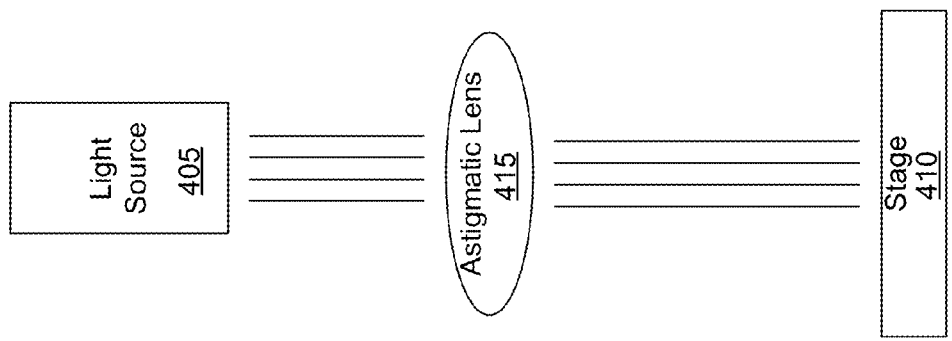

Reference will now be made to FIGS. 9a-9c. Light sources used in microscropy, particularly coherent light sources, may introduce spots or speckles to captured images. The present technology may avoid or reduce such speckling through the use of additional hardware. For example, in FIG. 9a, a quartz plate may be introduced between a light source 405 and a sample on a stage 410. It is noted that each of FIGS. 9a-9c may represent significant simplifications from actual implementations for purpose of illustration and are not intended to be limiting. The quartz plate may be an astigmatic lens 415. The astigmatic lens 415 may not possess figure-of-revolution symmetry and may result in distortion or aberration of light passing therethrough. Spinning or rotating the astigmatic lens 415 along an axis through or along which light passes may result in a general blurring of light passing through, or rather a homogenization of the light and a reduction of speckle potential.

Referring to FIG. 9b, a conduit 420, such as an optical fiber or other structure may be located between the light source 405 and the sample stage 410. While light passing through the optical fiber may not be exactly linear as illustrated in the figure, rays of light pass through the conduit in a similar manner over time and speckling may be present. FIG. 9c illustrates the use of a rotor, or alternately a motor 425 and a vibrator 430, to cause the conduit 420 to flex and change shape. For example, the vibrator may vibrate back and forth and may push or pull the conduit, causing a flexing or bending of the conduit, which may alter a path of light passing through the conduit. If the conduit is continuously flexed, then light exiting the conduit may appear more homogenous and include fewer speckles, thus improving overall image quality. As another example, a piston associated with the motor may be placed in proximity to the conduit to cause the conduit to move or oscillate, resulting in the light exiting the conduit increasing in homogeneity and decreasing in speckles to improve the resulting image quality.

The methods herein can also include creating a consistent light source using a technique of shaping the light source. The light source can be shaped by adjusting two sets of mirrors at a high speed fast enough to not be detected by the sCMOS camera. This can be done using two sets of two resonant scanners that are running at different speeds but locked together. Alternatively, such shaping can also be done with two fast 2 degree galvo mirrors that were also synchronized with each other. Other light shaping approaches can be similarly suitable. For example, the shaping may be performed using microelectromechanical systems (MEMS) mirrors.

Direct coupling of light to the microscope instead of a fiber can be useful to avoid laser loss. Furthermore, the method above can be used to create a square top or super-Gaussian output. This approach can also be coupled with a one or two position galvo mirror to cause the angle of the light going in to the objective to be at a TIRF position.

In yet another alternative, the method can also be adjusted so that the angle of the light going into the objective is at an oblique angle. This adjustment can be accomplished using a one or 2D galvo mirror.

The method above could be used to alternate quickly between the oblique angle and and a typical wide field illumination. In some situations this can create a field that could produce superior imaging or localization results in comparison to standard widefield imaging. Such improved localization or imaging would be in terms of better resolution and deeper depths. Angle switching (oblique widefield) can also lead to bleaching or putting the sample in dark or triple state. The angle switching method does not require a sCMOS camera and could also work with an EMCCD. The angle switching approach would also not require a linear module (i.e. quadfield).

For the method of imaging with a SCMOS camera the results can be improved by a variety of methods. Some of these methods may have significant imaging improvement for localization based imaging. One method to improve imaging efficiency include pre-filtering image data. For example, image data captured by the sensor may be pre-filtered before being stored or processed by the camera and/or before the image data is transmitted from the camera to a computing device for further processing. Various portions of the image data captured by the sensor may be devoid or substantially devoid of useful data. If the goal is to capture probe fluorescence and image data includes little to no fluorescence or other light (where "little" data may be defined as an amount of data below a defined threshold), pre-filtering of the image data may result in discarding of the image data with little to no fluorescence to speed up subsequent processing, storage, data transfer and other time consuming processes. These processes may be sped up due to a decrease in data to be processed resulting from the pre-filtering of the image data.

One method to improve imaging would be to improve the results for data received from the SCMOS camera. In one example, calibration of data can be taken with the camera and the corresponding light path. The calibration data could be taken such that each region on the camera would recording data for different imaging conditions. The region of the chip can be defined as individual pixels, groups of pixels that represent the typical size of a standard illuminated item (point spread function), or neighborhoods of pixels that would include several groups of pixels. The groups of pixels would typically be a grid pattern such as a 7×7 or 16×16 area, for example. The per-pixel calibration could be operated such that the middle pixel is surrounded by a group of pixels and neighborhood of pixels. A calibration could then be done on the whole field of the camera or only part of the camera. The groups or neighborhoods can optionally overlap.

Calibration imaging conditions can be adjusted and imaged independently and jointly. During the calibration various variables can be included such as, but not limited to, basic data, offset, gain, variance, and the like. The adjustment of the inputs could include (the Expanded Measures): the camera receiving different wave lengths of light (for examples 420, 520, 580, 670, 770 nm), including varying the light intensity; varying by ambient temperature; varying by length of imaging time (for example sub ms, to seconds); varying by imaging path components; varying by ambient light; varying the embedding medium; varying by sample holder type (example could include cover slip and slide, or 8 well container, or circular cover slip, or incubation chamber); as well as other items that would reasonably be expected to affect the outcome; and varying speeds of items moving across the screen for rolling shutter applications.

It is known that the SCMOS camera has more variation by pixel including the low noise level. One way to improve performance would be to measure the dark background of each pixel independently without a light source. It is also expected that there will be different ways to improve the results for improving the per pixel data (basic data) unrelated to the Expanded Measures enumerated above. For each pixel there can exist one more single or multivariable formulas to improve the per pixel data.

Using the Expanded Measures, separately, in groups or together one can create a set of correction factors for each pixel. The correction factors may be used in a multivariable formula to adjust the per pixel results. The results can also be combined with an expanded multivariable formula using both the basic data and the expanded measures. A two step process can also be used whereby the per-pixel data is first corrected using the basic formula and subsequently using a multivariable formula using adjusted correcting factors (reflecting for the basic data).

The factors and multi variable formulas can be based on mathematical or statistical approaches and may be simple to complex. The per-pixel changes can also be interchanged or complement with adjustments on a per group or neighborhood basis. For select microscopy imaging, including localization microscopy imaging further methods exists whereby the per-pixel is also adjusted for the rolling shutter variance required.

For example, a method of using a four field module for detecting sample luminescence can include: mounting a sample on a stage, the sample having a plurality of probe molecules; illuminating the sample with light to cause the probe to create luminescence; splitting the probe luminescence into at least four paths corresponding to at least four detection planes; detecting the at least four detection planes as a linear array via an sCMOS (scientific complementary metal-oxide-semiconductor) detector; recording the fields in corresponding linear recording regions of interest of the sCMOS detector; and combining a signal from the regions of interest into a two or three dimensional image.

This approach can be used to image two colors, two planes, but only focus on plane (2D current); two colors, one plane (2D); two colors, two planes (typical biplane); four colors (for TIRF would be 2 D only); four colors with astigmatism; two colors, two polarizations; two polarizations, two plains; 3 planes, 2 colors—1 primary focal plane (that is split in two colors)->two of the four planes, 2 additional focal planes; a module that uses some configuration to create an isotopic result; and a module that introduces PSF engineering in a different fashion.

In another example, rather than specifically using four paths to capture four detection planes, a method may use multiple paths (e.g., 2 or more) to capture one or more detection planes. Also, while various aspects of the present technology were described in the context of multi-path, multi-detection plane image capture, these aspects may be implemented independently of whether the image capture is performed in this manner. Specifically, the use of different linear regions on a rectangular image sensor to capture different detection or object planes, the use of color-weighting, the use of a rolling shutter with time delay compensation, pre-filtering of image data, MEMS mirrors, and as specific examples may be implemented independently of multi-path, multi-detection plane image capture. These aspects may further be implemented independently of one another.

While certain aspects of the present technology have been described in terms of use in fluorescent microscopy, the application of the present technology may not be limited to any particular field of study. For example, the present technology may be used in medical diagnostics or other industries as well. Specifically in such an application, and by way of non-limiting example, the probe molecules as described herein may correspond to molecules used to tag blood samples or the like. Some specific, non-limiting example molecules may include class I and class II molecules that are leczymes in humans and encoded by genes within the HLA-D region such as HLA-DP, HLA-DN, HLA-DM, HLA-DO, HLA-DQ or HLA-DR, or the various alleles of HLA-A, HLA-B and HLA-C loci, or the HLA-X, HLA-E, HLA-J, HLA-H, HLA-G and HLA-F genes.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method for creating three dimensional images using probe molecules, comprising:
   mounting a sample on a stage, the sample having a plurality of probe molecules;
   illuminating the sample with light to cause probe luminescence;
   splitting the probe luminescence into multiple paths corresponding one or more detection planes corresponding to object planes in the sample;
   detecting the one or more detection planes as a linear array via an sCMOS (scientific complementary metal-oxide-semiconductor) detector, wherein detecting the at least one or more detection planes via the sCMOS detector comprises detecting each detection plane in a different linear region of the sCMOS detector, and wherein the sCMOS detector comprises a rectangular sensor;
   recording the object planes in corresponding linear recording regions of interest of the sCMOS detector; and
   combining a signal from the regions of interest into a two or three dimensional image.

2. A method in accordance with claim 1, further comprising dichroically separating the probe luminescence into at least two wavelengths of light prior to or after splitting the probe luminescence, and wherein a first at least two of the multiple paths into which the probe luminescence is split correspond to a first wavelength of the at least two wavelengths, and a second at least two paths of the multiple paths into which the probe luminescence is split correspond to a second wavelength of the at least two wavelengths.

3. A method in accordance with claim 1, wherein illuminating the sample with light further comprises illuminating the sample with an activation light to activate at least one subset of the plurality of probe molecules, and subsequently illuminating the sample with an excitation light to cause probe luminescence.

4. A method in accordance with claim 1, further comprising separately recording the object planes for different regions of the sample and arranging the recording planes for the different regions together as a composite two or three dimensional image based on a different-wave length weighted calibration offset.

5. A method in accordance with claim 1, further comprising blurring the light using a blurring device between a light source and the stage.

6. A method in accordance with claim 5, wherein the blurring device comprises a vibration motor configured to vibrate and cause movement of a light guide to disrupt the light passing through the light guide.

7. A method in accordance with claim 1, further comprising forming a consistent light source by shaping the light source.

8. A method in accordance with claim 7, wherein the shaping is accomplished using a set of locked resonant scanners running a different speeds.

9. A method in accordance with claim 7, wherein the shaping is accomplished using microelectromechanical systems (MEMS) mirrors.

10. A method in accordance with claim 4, wherein the blurring device comprises an astigmatic lens or a photomask oriented between the between an objective and the sCMOS camera to enable point spread function engineering.

11. A method in accordance with claim 1, further comprising combining a two class calibration to create improved imaging data.

12. The method in accordance with claim 11, wherein the two class calibration corresponds to a first class of parameters specific to the sensor used in the detector and a second class of parameters related to typical imaging conditions.

13. The method claim 11, wherein classes of parameters in the two class calibration are determined based on characteristics of a microscopy system for performing the method on a onetime or regular basis.

14. The method of claim 11, wherein either class of the two class calibration is processed as part of post processing at or near the sCMOS detector before being transferred to a computer.

15. The method of claim 14, wherein the processing near the detector is performed by a processor embedded in an integrated circuit.

16. The method of claim 14, wherein the imaging data with irrelevant to the microscopy imaging is removed through pre-filtering prior to being transferred to a computer.

17. The method of claim 14, wherein the imaging data is adjusted to compensate for effects of a rolling shutter of the sCMOS detector.

18. The method of claim 11, wherein the two class calibration adjusts for wavelength of light or light intensity or length of per frame imaging time.

19. The method of claim 11, wherein the two class calibration adjusts for sample and imaging conditions of ambient light or embedding medium or cover slip or temperature.

20. The method of claim 11, wherein the two class calibration is dependent on the behavior of pixels within a neighborhood.

21. A method in accordance with claim 1, further comprising operating the sCMOS detector in a rolling shutter mode and compensating for a time delay resulting from rolling of a shutter of the sCMOS detector.

22. A method for creating three dimensional images using probe molecules, comprising:
   mounting a sample on a stage, the sample having a plurality of probe molecules;
   illuminating the sample with light to cause probe luminescence;
   splitting the probe luminescence into multiple paths corresponding one or more detection planes corresponding to object planes in the sample;
   detecting the one or more detection planes as a linear array via an sCMOS (scientific complementary metal-oxide-semiconductor) detector;
   recording the object planes in corresponding linear recording regions of interest of the sCMOS detector; and
   combining a signal from the regions of interest into a two or three dimensional image, wherein the recording includes separately recording the object planes for different regions of the sample and the combining includes arranging the recording planes for the different regions together as a composite two or three dimensional image based on a different-wave length weighted calibration offset.

23. A method in accordance with claim 22, wherein detecting the at least one or more detection planes via the sCMOS detector comprises detecting each detection plane in a different linear region of the sCMOS detector, and wherein the sCMOS detector comprises a rectangular sensor.

24. A method in accordance with claim 22, further comprising blurring the light using a blurring device between a light source and the stage.

25. A method in accordance with claim 22, further comprising combining a two class calibration to create improved imaging data.

26. A method in accordance with claim 22, further comprising operating the sCMOS detector in a rolling shutter mode and compensating for a time delay resulting from rolling of a shutter of the sCMOS detector.

27. A method in accordance with claim 1, wherein illuminating the sample with light further comprises illuminating the sample with an activation light to activate at least one subset of the plurality of probe molecules, and subsequently illuminating the sample with an excitation light to cause probe luminescence.

28. A method for creating three dimensional images using probe molecules, comprising:
   mounting a sample on a stage, the sample having a plurality of probe molecules;
   illuminating the sample with light to cause probe luminescence;
   splitting the probe luminescence into multiple paths corresponding one or more detection planes corresponding to object planes in the sample;
   detecting the one or more detection planes as a linear array via an sCMOS (scientific complementary metal-oxide-semiconductor) detector;
   recording the object planes in corresponding linear recording regions of interest of the sCMOS detector; and
   combining a signal from the regions of interest into a two or three dimensional image, wherein the combining includes a two class calibration to create improved imaging data, wherein either class of the two class calibration is processed as part of post processing at or near the sCMOS detector before being transferred to a computer.

29. A method in accordance with claim 28, wherein illuminating the sample with light further comprises illuminating the sample with an activation light to activate at least one subset of the plurality of probe molecules, and subsequently illuminating the sample with an excitation light to cause probe luminescence.

30. A method in accordance with claim 28, further comprising separately recording the object planes for different regions of the sample and arranging the recording planes for the different regions together as a composite two or three dimensional image based on a different-wave length weighted calibration offset.

31. A method in accordance with claim 28, further comprising blurring the light using a blurring device between a light source and the stage.

* * * * *